United States Patent [19]

Heckele et al.

[11] Patent Number: 5,620,440
[45] Date of Patent: Apr. 15, 1997

[54] MEDICAL INSTRUMENT FOR APPLYING HOT GAS

[75] Inventors: Helmut Heckele, Knittlingen; Manfred Boebel, Ötisheim; Detlev Branscheid, Ahrensburg, all of Germany

[73] Assignee: Richard Wolf GmbH, Knittlingen, Germany

[21] Appl. No.: 338,331

[22] Filed: Nov. 14, 1994

[30] Foreign Application Priority Data

Nov. 13, 1993 [DE] Germany ............ 43 38 866.3

[51] Int. Cl.⁶ .................................. A61B 17/36
[52] U.S. Cl. .................. 606/28; 606/27; 606/40; 606/49; 604/26
[58] Field of Search ............... 606/1, 27–31, 606/40, 49; 607/96, 98, 99; 392/379, 380, 383–385, 409, 410; 604/26, 23

[56] References Cited

U.S. PATENT DOCUMENTS

| 319,698 | 6/1885 | Graefe | 606/28 |
|---|---|---|---|
| 3,434,476 | 3/1969 | Shaw et al. | 606/27 |
| 4,796,622 | 1/1989 | Lu et al. | 606/28 |
| 5,444,215 | 8/1995 | Bauer | 392/380 |

*Primary Examiner*—Angela D. Sykes
*Assistant Examiner*—Michael Peffley
*Attorney, Agent, or Firm*—Cohen, Pontani, Lieberman, Pavane

[57] ABSTRACT

There is disclosed an instrument for applying hot gas for medical purposes having a heating device for heating up gas which is conducted by means of a fan through a first channel to the distal end of the instrument, where the gas is diverted through a second channel of the instrument and back to the heating device and fan.

13 Claims, 5 Drawing Sheets

MEDICAL INSTRUMENT FOR APPLYING HOT GAS

FIELD OF THE INVENTION

The invention relates to an instrument for the application of hot gas for medical purposes, in particular for the heat treatment and coagulation of tissue, having a heating device for heating up gas which is conducted through a channel to the distal end of the instrument.

BACKGROUND OF THE INVENTION

In endoscopy it is frequently necessary to heat tissues selectively for local application of heat or for coagulation, wherein basically a distinction is to be made between methods in which heat transfer takes place with direct contact of the tissue and methods in which heat transfer to the tissue takes place indirectly.

For instance, in DE-A-3 642 077 there is disclosed a device for high-frequency cutting and/or coagulation or for laser application. A further electrosurgical coagulation device is known from DE-A-3 710 489. Finally, from open surgery are also known cauterising tools for coagulation by means of gases, for example from EP-A-0 447 121 or from DE-C-75 016.

In the endoscopic use of such heat applying or coagulating instruments, the instrument for regional treatment of the body cavity with heat is for example introduced into the body cavity by a trocar. In such interventions the body cavity is frequently expanded, for which purpose gases are used, the gases being conducted under excess pressure into the body cavity. In coagulation by means of the above-mentioned devices, gases are produced which must be extracted from the body cavity, as they impair the view of the surgeon. In order to maintain the expansion of the body cavity, frequent postinsufflation of the supporting gas is therefore necessary.

In endoscopic use, the adaptation of gas coagulators of the kind described above does not offer a solution avoiding the disadvantages stated, because such devices in particular also have the disadvantage that in the case of incomplete combustion of the combustible gases used an explosive mixture can be formed. In the case of the subject according to DE-C-75 016 this mixture could be caused to explode by the open flame, or in a device according to EP-A-0 447 121 an explosion could be brought about due to arcing by the electrodes. Moreover with these methods residues would be formed by combustion of the gases, which would have to be removed very carefully from the body cavity.

The above-mentioned disadvantages concern first and foremost requirements connected with the necessary extraction of smoke and maintenance of the body cavity expansion. The disadvantages of electrically operated coagulating devices lie in particular in that basically an electrical potential is applied to the patient, owing to which in case of any breakdowns of the electrical system, for example due to insulation faults, there can be considerable danger to the patient. Potential-free systems such as laser coagulators are by contrast very elaborate and difficult to handle.

SUMMARY OF THE INVENTION

An object of the invention is to provide a hot gas applicator for regional heating and/or coagulation, in which an electrical potential which may possibly endanger the patient is not used and during application thereof the formation of explosive gas mixtures in the body cavity is prevented. Furthermore the gas pressure prevailing in the body cavity during application of this instrument should not be affected and a simple and cheap construction of the instrument should be made possible.

According to the invention in an instrument of the aforementioned kind, the gas is forced by means of a fan in circulation through the above-mentioned channel to the distal end of the instrument, and there with a diversion passes into a further channel and is conducted back to the heating device and the fan.

The advantages that can be obtained with this construction lie in particular in that the parameters of gas pressure and gas composition are preserved unchanged at the point of treatment during application.

The first channel which conducts the gas to the distal end of the instrument and the second channel which returns the gas to the fan may be formed by tubes extending coaxially with each other and together forming a shaft having inner and outer tubes, wherein the inner tube serves to supply gas, so that homogeneous gas conduction and favorable energy conversion are obtainable. In this case precise temperature regulation can be achieved by temperature sensing means which is arranged in each channel and which is connected to control means, this being in particular if the temperature sensing means is arranged in each case in the distal region of the channels. Aggregation, which is advantageous from the practical point of view, results if the fan, a drive thereof and the control means as well as the heating means are accommodated together in a handle of the instrument. By designing the handle with a releasable shaft and a removable electrical section, optimum conditions are fulfilled for disassembling and sterilising the whole system.

According to a further advantageous embodiment, the distal end of the shaft can be provided with different nozzles or with a closed coagulating end piece. Thus there is a possibility of adapting the instrument to different requirements, for example for carrying out multi-plane coagulations. Moreover for the purpose of keeping the system free from moisture from the body cavity, moisture filter means can be provided in the second channel as well as pressure relief valve means for avoiding inadmissible pressure increases in the body cavity. Finally the inner tube and the outer tube can be arranged axially slidably relative to each other, as a result of which on the one hand a tissue surface to be heated or coagulated can be treated with the hot gas from different distances and on the other hand nozzles of different constructions can be mounted as coagulating end pieces on the same shaft.

DETAILED DESCRIPTION OF PREFERRED EMBODIMENTS OF THE INVENTION

Figure 1:
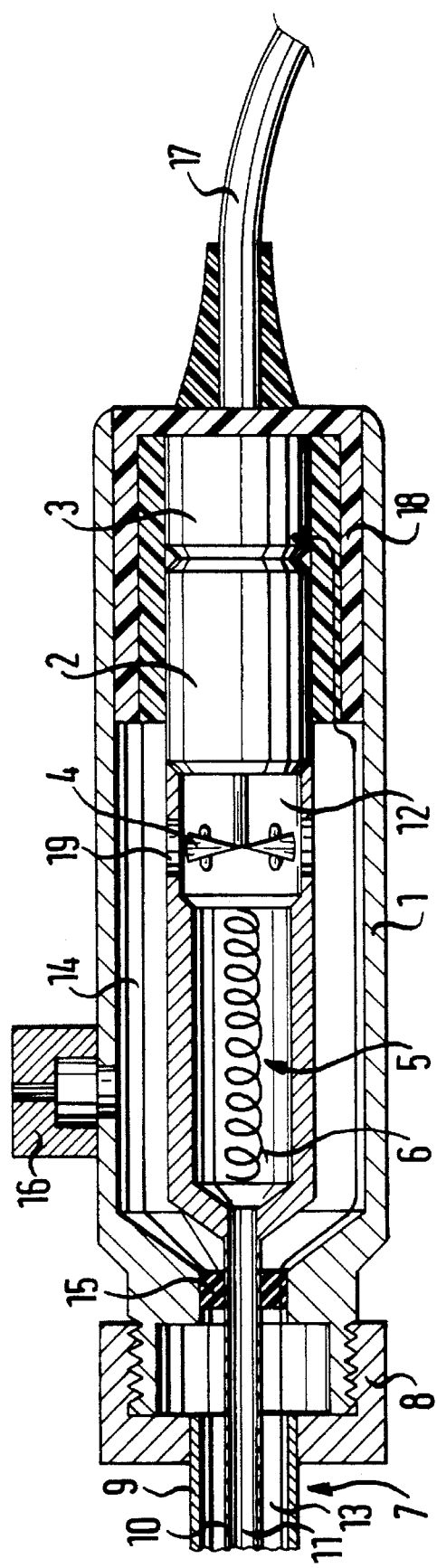
FIG. 1 is a longitudinal section through the handle of the hot gas applicator according to the invention.

The hot gas applicator according to the invention essentially consists of an electric motor 2 accommodated in a handle 1 with electronic control means 3 for the calorific output and a fan 4 which is adjoined by a heating device 5 with a heating coil 6. At the distal end of the instrument, a double-walled shaft 7 is mounted releasably on the handle 1 with a union nut 8.

Figure 2:
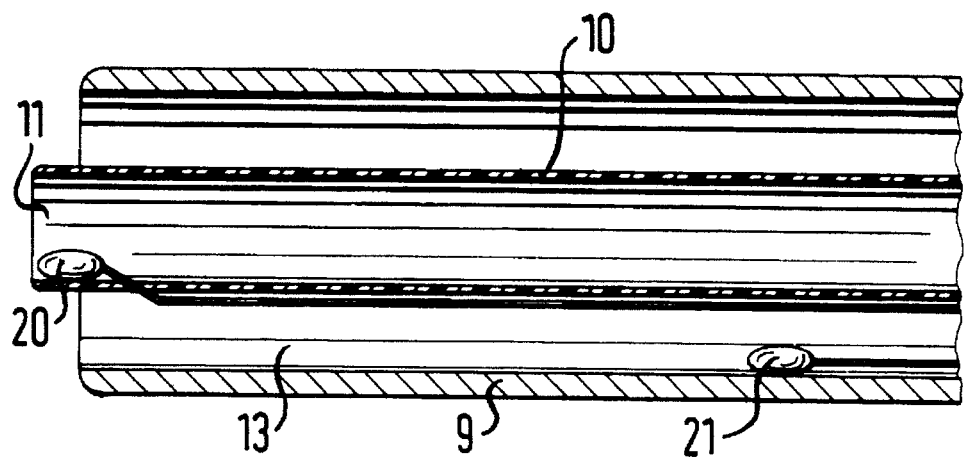
FIG. 2 is a longitudinal section through the distal end region of the applicator according to FIG. 1.

As can be seen from FIG. 2, the shaft 7 has an outer tube 9 in which an inner tube 10 is guided. The inner tube 10 forms a supply channel 11 which is connected to the delivery side of the fan 4 or to a chamber 12 surrounding the fan 4 and the heating device 5 and serves to conduct the heated gas to the distal end of the instrument. The outer tube 9 forms with the inner tube 10 a channel 13 of annular cross-section which opens into a chamber 14 which is formed by the handle 1 and communicates with the intake side of the fan 4.

The shaft 7 which can be mounted releasably on the handle 1 of the hot gas applicator can be of different construction in its distal end region. Thus according to FIG. 4 the outer tube 9 and the inner tube 10 are curved, wherein the inner tube 10 protrudes at its distal end 25 relative to that of the outer tube 9. According to FIG. 5 the shaft is provided with an outer tube 9 which is sealed at the end face in its distal end region and constructed with a lateral opening 26. The inner tube 10 is in this case curved in its distal end region and ends in the lateral opening 26, wherein the distal end 27 of the inner tube 10 is set back within the opening 26.

Figure 6:
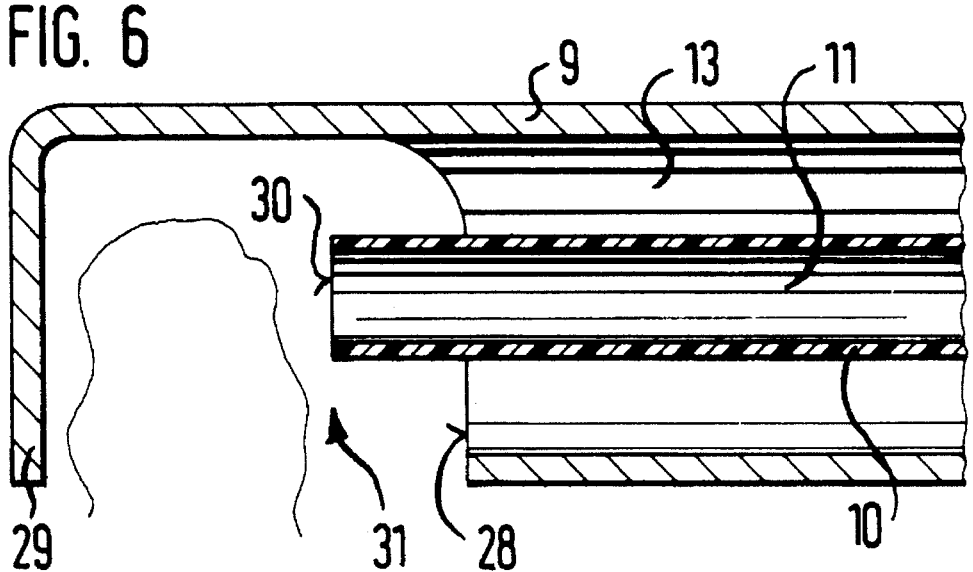
FIG. 6 is a view corresponding to FIG. 2 with a shaft designed with a shield at the distal end.
Figure 7:
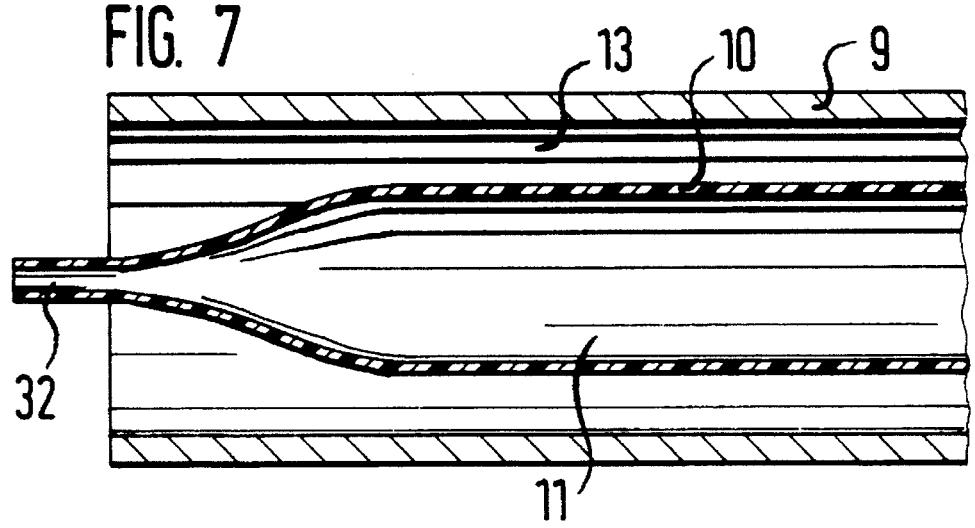
FIG. 7 is a view corresponding to FIG. 2 with a nozzle of reduced cross-section arranged at the distal end.
Figure 8:
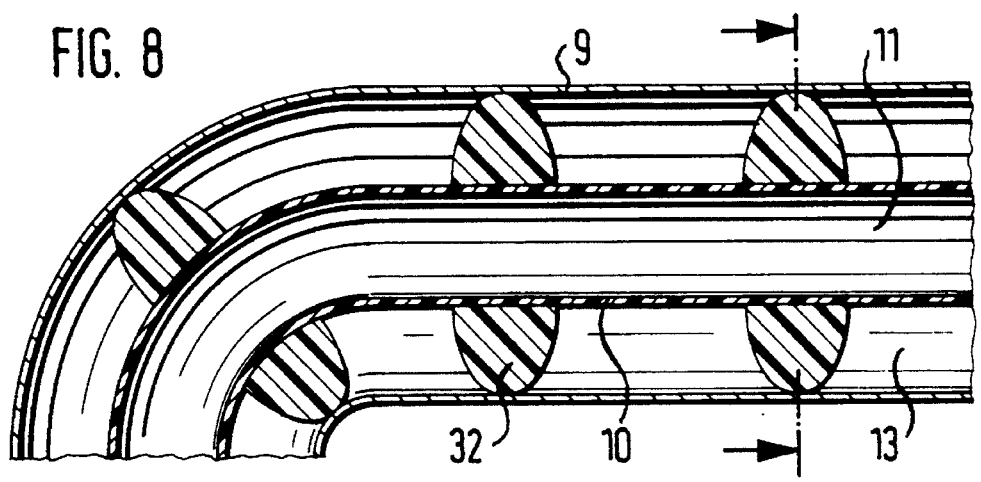
FIG. 8 is a view corresponding to FIG. 2 with a shaft of flexible construction.
Figure 8A:
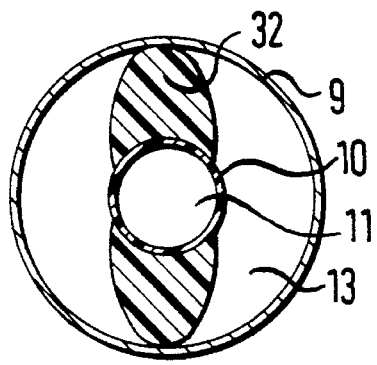
FIG. 8a is a cross-section through the shaft according to FIG. 8.
Figure 9:
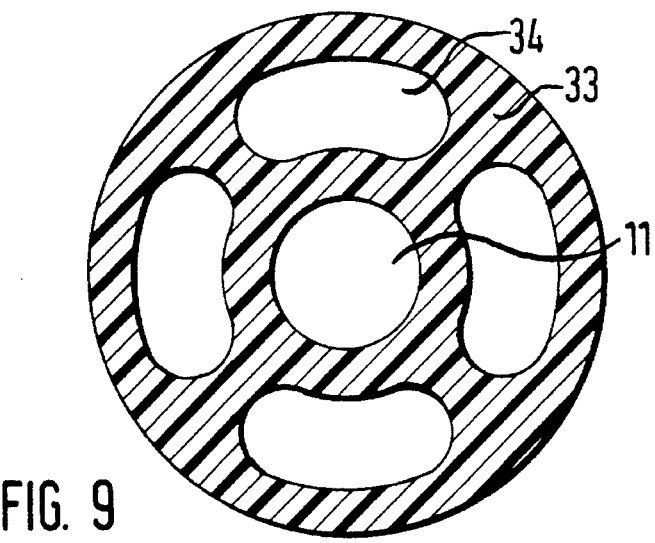
FIG. 9 is a cross-section through a flexible shaft of modified construction.

In the construction according to FIG. 6, opposite the distal end 28 of the outer tube 9 is a shield 29 connected thereto, and the distal end 30 of the inner tube 10 extends into a gap 31 between the distal end 28 of the outer tube 9 and the shield 29. The construction according to FIG. 7 differs from the one according to FIG. 2 only in the design of the inner tube 10, of which the distal end is constructed as a nozzle 32 of narrower cross-section. Finally the construction according to FIG. 8 involves a flexible shaft in which projections 32 between inner tube 10 and outer tube 9 ensure mutual support thereof and coaxial guiding relative to each other. The outer tube 9 and the inner tube 10 are in this case made of suitable plastic, wherein materials used for example with catheters can be used. The cross-section shown in FIG. 9 shows an alternative embodiment of the flexible shaft made by extrusion, in which is used a tube profile 33 which encompasses the supply channel 11 and the channel 13 for the hot gas return, the channel 13 being formed from several partial channels 34.

A moisture filter 15 passes through the channel 13 according to FIG. 1, and the chamber 14 is provided with a pressure relief valve 16. The electric motor 2, the control means 3 and the connecting cable 17, i.e. the potential-carrying parts, are accommodated as shown in FIG. 1 in a separate support 18 which can be releasably connected to the handle 1 in a suitable manner. Finally as can be seen from FIG. 2 temperature sensors 20 and 21, are arranged in the distal region of the channels 11 and 13 in the inner tube 10 and outer tube 9 respectively.

When using the hot gas applicator according to the invention, it is applied via a puncture wound to the point of the body cavity to be treated, and then the body cavity gas is blown by the fan 4, which is operated by means of the electric motor. 2, over the heating coil 6 of the heating device 5 and is heated. The heated gas then flows out in the distal direction through the inner tube 10 of the shaft forming the supply channel 11, to the tissue region to be heated or coagulated. At the same time extracted body cavity gas flows from the place of treatment back through the channel 13 between inner tube 10 and outer tube 9 and, after passing through the chamber 14, flows via gas inlet openings 19 into the housing of the fan 4 and from there, closing the circuit, back over the heating coil 6 into the body cavity.

With this type of heating or coagulation of tissue, no smoke gases which would have to be extracted are produced during operation, on account of which the respective body cavity pressure will also as a rule remain unchanged. Due to gas return via the channel 13 between inner tube 10 and outer tube 9 of the shaft, as a further advantage, no high temperatures can arise on the outer wall of the outer tube 9. Moreover further temperature compensation is achieved by the additional intake of ambient air or body cavity gas.

The temperature sensors 21, 20 are arranged on the inside of the outer tube 9 of the shaft or on the inside of the inner tube 10 and connected to the control means 3 in the handle 1. With this construction the coagulation or heating temperature can always be adjusted, depending on the application, and in particular the temperature of the outer tube 9 can be limited to a physiologically acceptable value, e.g. 40° C.

The process is further controlled by the pressure relief valve 16 which responds on exceeding a predetermined system pressure and opens temporarily, so that there cannot be inadmissible pressure rises inside the body cavity. Finally the moisture filter 15, which can be made of commercially available woven material and which lets moisture pass in only one direction, ensures that moisture from the body cavity is kept away from the gas circuit.

As described above, the handle 1 can be separated from the shaft 7 by unscrewing the union nut 8. This and the releasability of the support 18 with the potential-carrying parts of the applicator instrument allow optimum disassembling and sterilisability of the whole system.

Use of the hot gas applicator according to the invention takes place particularly advantageously without contact, wherein by changing corresponding nozzles which can be fitted onto the distal end piece of the shaft or otherwise fixed, in particular plane coagulation can be carried out.

Figure 3:
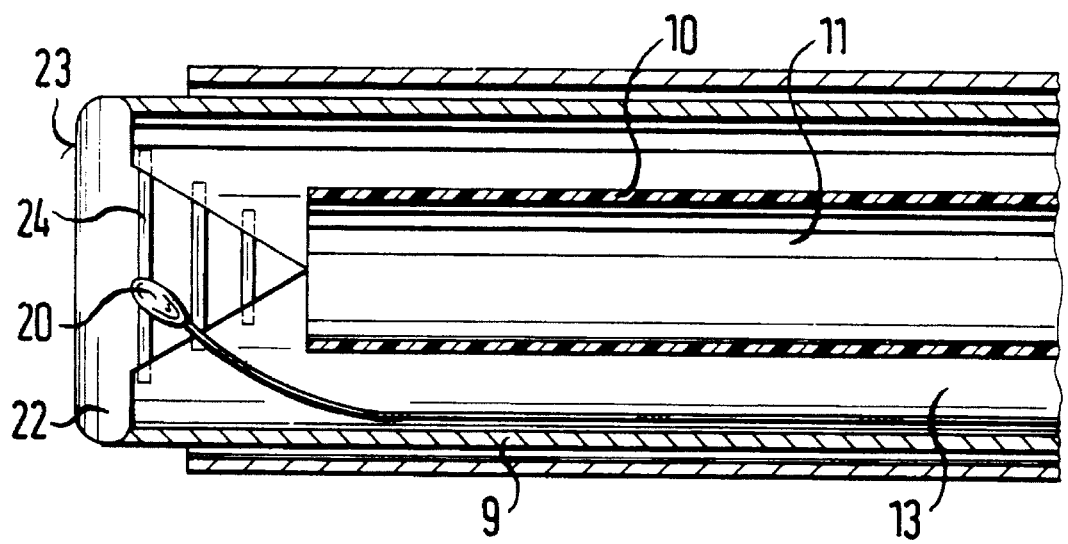
FIG. 3 is a longitudinal section through the applicator corresponding to FIG. 2 with a modified end piece.

Furthermore it is also possible, for carrying out contact coagulation, to place a closed coagulating end piece 22 as shown in FIG. 3 on the distal end instead of an open nozzle. This coagulating end piece 22 is provided at the distal end with a non-stick coating 23 and advantageously constructed in cone form at the proximal end and arranged in such a way that the centre axes of the coagulating end piece 22 and of the inner tube 10 are aligned with each other, as a result of which favorable flow around the coagulating end piece 22 to be heated and satisfactory return flow of the hot gas within the annular channel 13 between the inner tube 10 and the outer tube 9 of the shaft are ensured. By providing the conical portion of the coagulating end piece 22 which is exposed to the hot gas stream with lamellae 24, improved heat exchange is achieved due to the increased area of contact. In the construction with a coagulating end piece 22, the temperature sensor 20 for control of the temperature of the hot gas is advantageously mounted in the region of the cone of the coagulating end piece 22, while the temperature sensor 21 for control of the maximum permitted outside temperature of the outer tube 9 of the shaft is arranged at approximately the same point as in the practical example according to FIG. 2.

With selective use of the variants of the shaft shown in FIGS. 4 to 8, the applicator described can be adapted according to the respective requirements.

Figure 4:
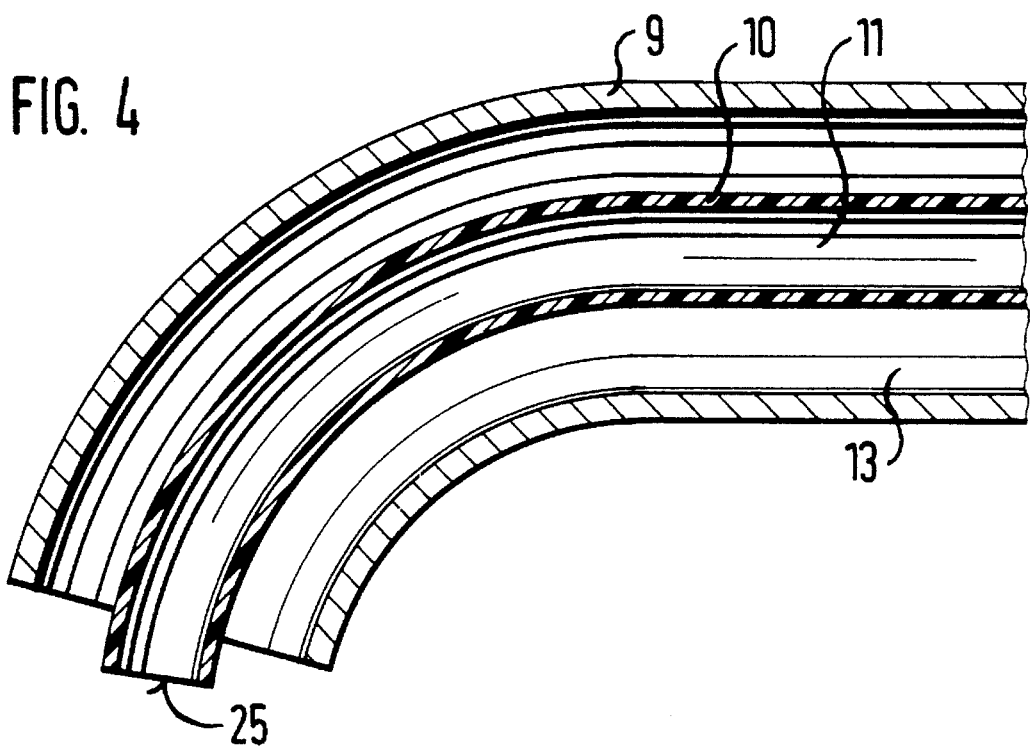
FIG. 4 is a view corresponding to FIG. 2 with a curved shaft in the distal end region.
Figure 5:
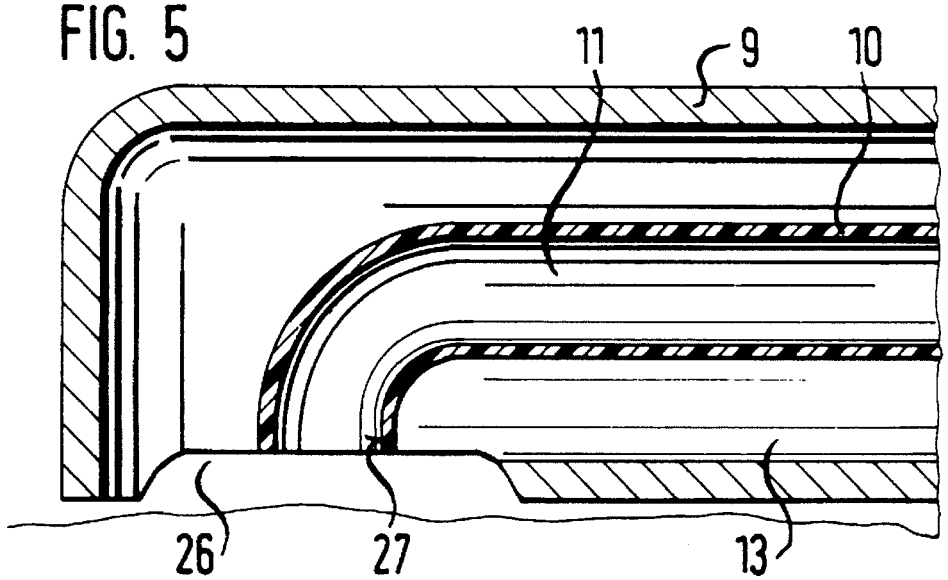
FIG. 5 is a view corresponding to FIG. 2 with a shaft designed with a lateral opening in the distal end region.

Thus the construction according to FIG. 4 allows lateral coagulation of tissue, wherein with the construction according to FIG. 5 coagulation focused more on certain points can be carried out, which is achieved by the fact that, when the outer tube 9 of the shaft is placed on the tissue, the inner tube 10 conducting the hot gas remains spaced apart from the tissue. With the construction according to FIG. 6 it is possible to engage behind tissue and coagulate tissue selectively, wherein the shield 29 which engages at the back simultaneously ensures the protection of tissue behind it. A further refinement with respect to coagulation of a precise point is possible with the construction according to FIG. 7. Finally with the flexible construction of the shaft according to FIGS. 8 and 9 there is the possibility of adapting the applicator by simple deformation of such a shaft to diverse circumstances.

What is claimed is:

1. An instrument for applying hot gas for heat treatment and coagulation of tissue in a body cavity, comprising:

a double-walled shaft forming two coaxial tubes which respectively define a first channel and a second channel, the shaft having a proximal end and a distal end;

heating means arranged at the proximal end of the shaft for heating up insufflation gas in the body cavity;

fan means arranged at the proximal end of the shaft for drawing the gas into an outer one of the tubes at the distal end of the shaft, back through the outer tube to the heating means and fan means at the proximal end of the shaft, and circulating the heated gas through an inner one of the tubes from the proximal end to the distal end; and temperature sensing means arranged in each of the tubes for sensing gas temperature within the tubes.

2. The instrument according to claim 1, wherein the temperature sensing means are arranged near the distal end of the shaft.

3. The instrument according to claim 1, and further comprising a handle connected to the proximal end of the shaft, the fan means and the heating means being arranged within the handle.

4. The instrument according to claim 1, wherein the handle and the proximal end of the shaft are releasably connected together.

5. The instrument according to claim 1, wherein the distal end of the shaft is formed as a nozzle.

6. The instrument according to claim 1, wherein the outer tube and the inner tube of the shaft each have a curved distal end, the distal end of the inner tube being configured to protrude from the distal end of the outer tube.

7. The instrument according to claim 1, wherein the outer tube has a distal end which is sealed and provided with a lateral opening and the inner tube has a distal end which is curved and set back within the lateral opening.

8. The instrument according to claim 1, wherein the outer tube has a distal end and a shield located opposite said distal end so as to form a gap, and the inner tube has a distal end which extends into the gap.

9. The instrument according to claim 1, wherein the outer tube and the inner tube are flexible and further comprising projection means for guiding the inner tube coaxially relative to the outer tube.

10. The instrument according to claim 9, wherein the flexible shaft is formed from a hollow plastic profile which forms the first and second channels and the second channel comprises several partial channels.

11. The instrument according to claim 1, and further comprising a closed coagulating end piece at the distal end of the shaft.

12. The instrument according to claim 1, and further comprising moisture filter means and pressure relief valve means, said moisture filter means being located in said second channel and being connected to said valve means.

13. The instrument according to claim 1, wherein the inner tube and the outer tube are arranged axially slidably relative to one another.

* * * * *